United States Patent
Ardanese et al.

(10) Patent No.: US 12,051,786 B2
(45) Date of Patent: Jul. 30, 2024

(54) HIGH THROUGHPUT EXTRACTION OF BATTERY CELL FORMATION GAS

(71) Applicant: GM GLOBAL TECHNOLOGY OPERATIONS LLC, Detroit, MI (US)

(72) Inventors: Raffaello Ardanese, Bloomfield Hills, MI (US); Thomas A. Yersak, Royal Oak, MI (US); James R. Salvador, East Lansing, MI (US); Ryan Curtis Sekol, Grosse Pointe Woods, MI (US); Dmitriy Bruder, Clinton Township, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 356 days.

(21) Appl. No.: 17/543,864

(22) Filed: Dec. 7, 2021

(65) Prior Publication Data
US 2023/0178816 A1 Jun. 8, 2023

(51) Int. Cl.
*H01M 10/42* (2006.01)
*G01N 1/22* (2006.01)
*G01N 33/00* (2006.01)

(52) U.S. Cl.
CPC ...... *H01M 10/4285* (2013.01); *G01N 1/2226* (2013.01); *G01N 33/0009* (2013.01); *G01N 2001/2241* (2013.01)

(58) Field of Classification Search
CPC ........... H01M 10/4285; H01M 4/0447; H01M 10/48; H01M 50/30; H01M 10/446;
(Continued)

(56) References Cited

U.S. PATENT DOCUMENTS

2012/0070703 A1* 3/2012 Wahl ................... H01M 50/213
429/82
2015/0089998 A1* 4/2015 Tipler ................... G01N 30/66
73/23.42
(Continued)

FOREIGN PATENT DOCUMENTS

JP 2001332312 A * 11/2001
JP 2017009539 A * 1/2017

OTHER PUBLICATIONS

JP-2017009539-A-Translated (Year: 2017).*
JP-2001332312-A-Translate (Year: 2001).*

*Primary Examiner* — Kristina M Deherrera
*Assistant Examiner* — Fatemeh Esfandiari Nia
(74) *Attorney, Agent, or Firm* — CANTOR COLBURN LLP

(57) ABSTRACT

Aspects of the disclosure include degas equipment and degassing process schemes for providing high throughput extraction of battery cell formation gas. An exemplary method can include loading a battery cell in a sampling chamber of a degas station and creating an opening in the battery cell to release formation gas. A first portion of the formation gas can be routed to a collection chamber of the degas station while the formation gas is prevented from venting. After routing the first portion of the formation gas to the collection chamber, a second portion of the formation gas can be vented until degassing is complete. The first portion of the formation gas can be diluted with a dilution fluid and the diluted first portion of the formation gas can be routed to a cell quality control gas manifold configured to measure battery cell formation gas compositions.

18 Claims, 8 Drawing Sheets

(58) Field of Classification Search
CPC . H01M 10/0525; Y02E 60/10; G01N 1/2247; G01N 1/34; G01N 1/2226; G01N 2001/2241
See application file for complete search history.

(56) References Cited

U.S. PATENT DOCUMENTS

2020/0176833 A1* 6/2020 Hwang ............. H01M 10/4207
2020/0227709 A1* 7/2020 Dittel ................. H01M 10/052

* cited by examiner

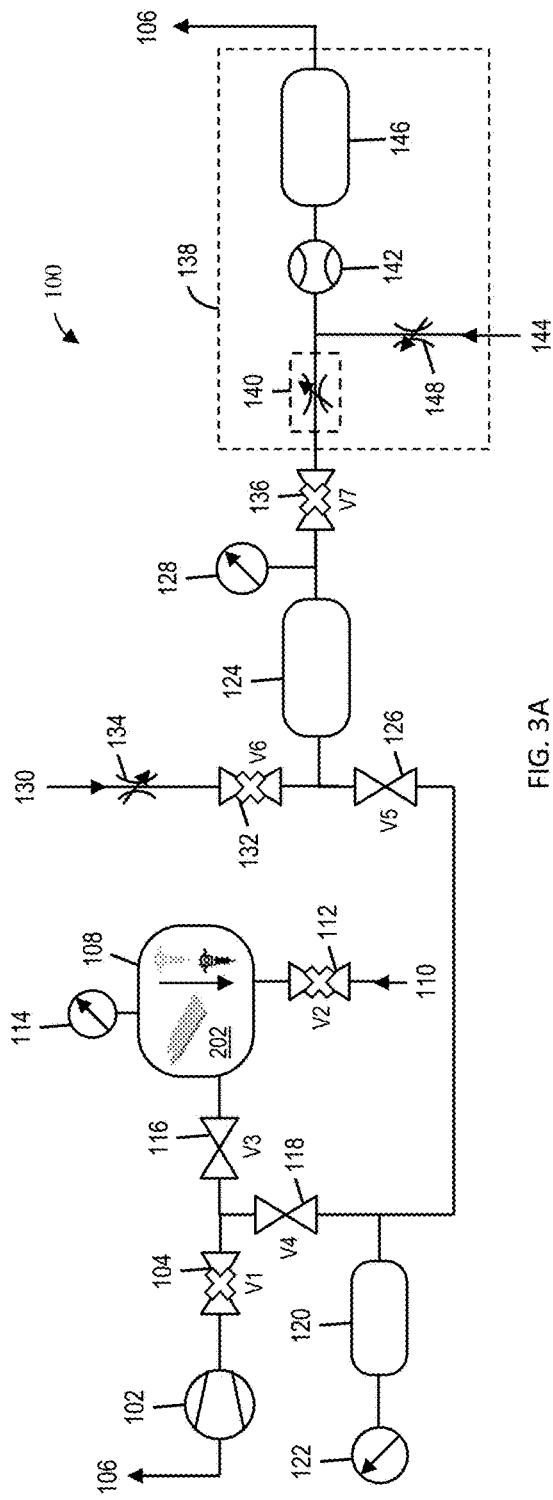
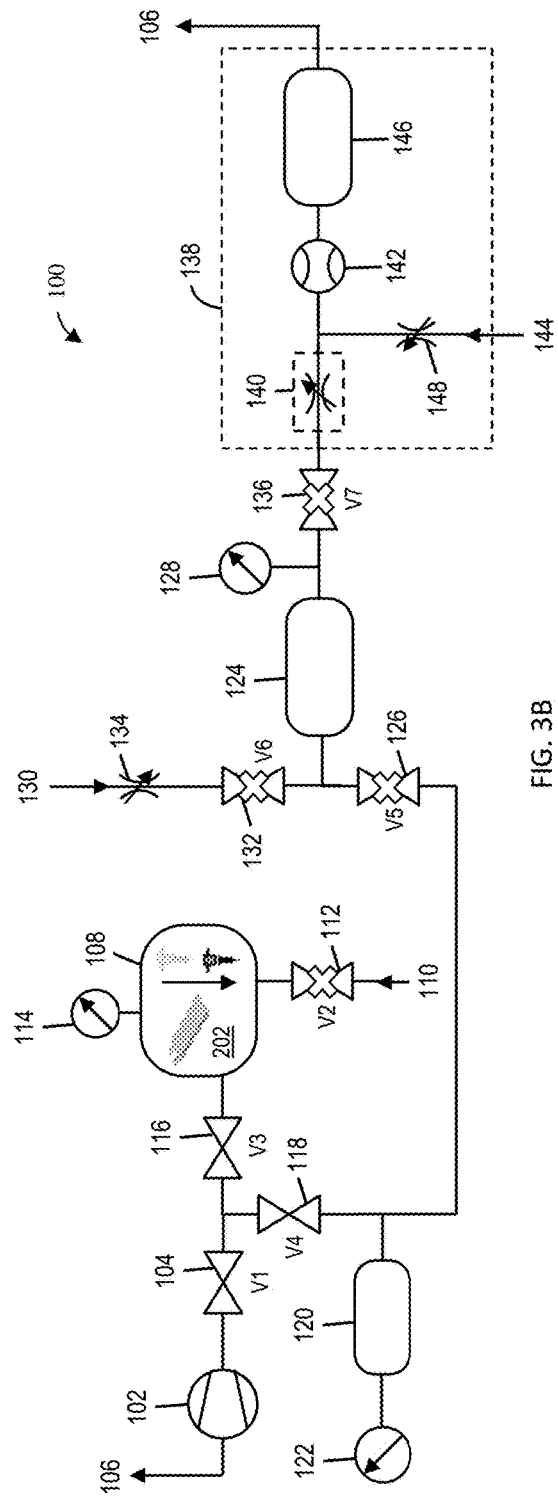
FIG. 3A
FIG. 3B

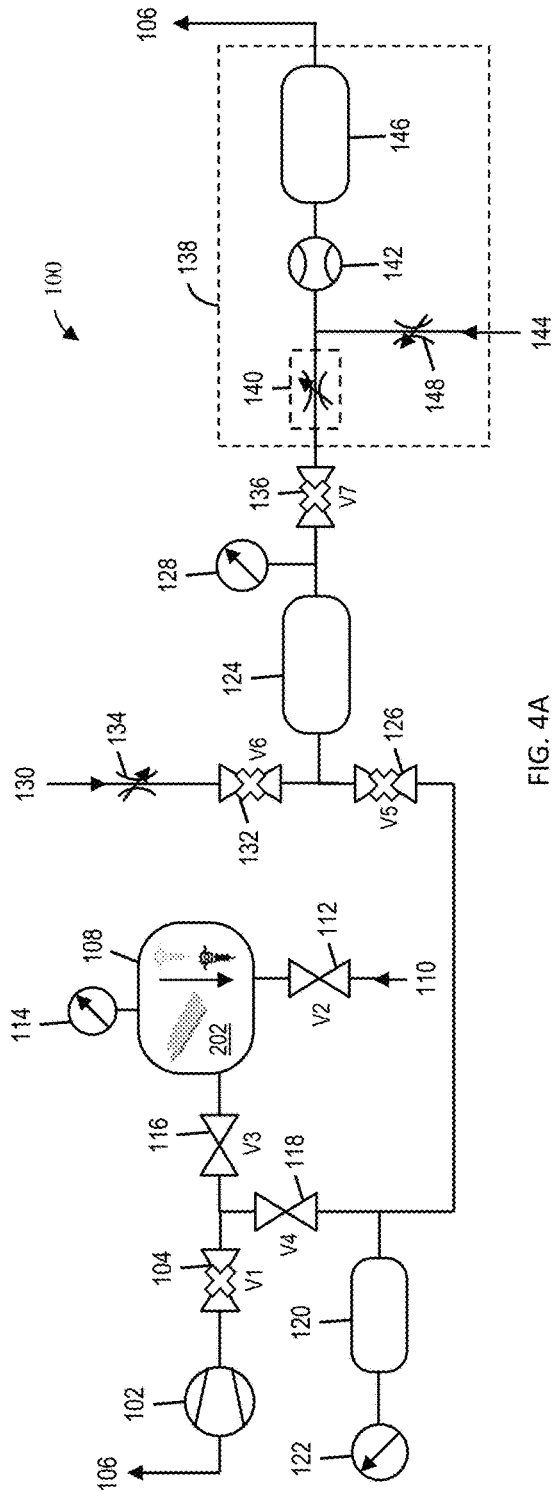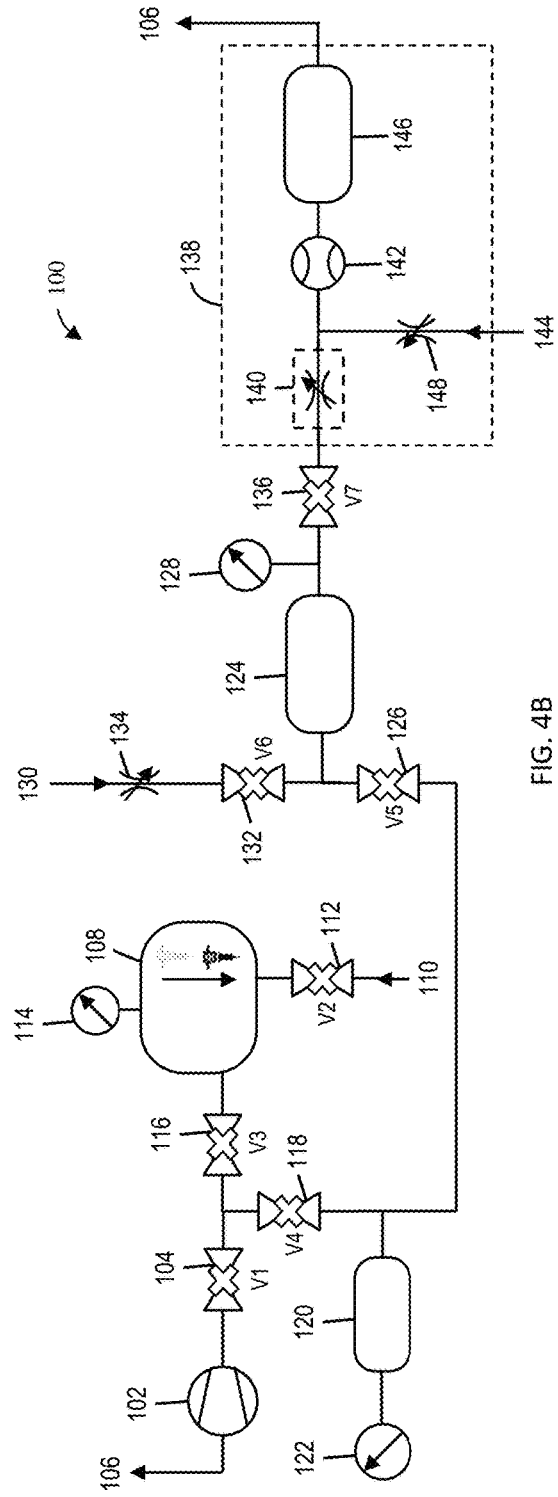
FIG. 4A
FIG. 4B

HIGH THROUGHPUT EXTRACTION OF BATTERY CELL FORMATION GAS

The present disclosure relates to battery cell manufacturing, and particularly to the high throughput extraction of battery cell formation gas.

Lithium-ion batteries are one of the most commonly used energy storage technologies with applications ranging from small portable electronics to large electric vehicle battery packs. Lithium-ion batteries have become increasingly favored as a battery platform due to various desirable electrical energy storage characteristics, such as, for example, energy density, power density, maximum charging rate, internal leakage current, equivalent series resistance (ESR), charge-discharge cycle durability, and high electrical conductivity. The development of scalable, highly efficient next-generation lithium-ion battery manufacturing capabilities is critical to further advances in portable electronic devices and the implementation of high-efficiency electric vehicles.

During battery construction the battery cells must undergo a formation process which, besides the raw material cost, is the most expensive step in battery manufacturing. Within the formation process battery cell surface interfaces are grown to stabilize the electrolyte against the anode electrode (e.g., lithiated graphite). The electrolyte decomposes upon the anode surface, resulting in the formation of a solid electrolyte interface (SEI) layer. The SEI layer acts as a protective layer to prevent continuous electrolyte decomposition and solvent co-intercalation into graphitic layers during subsequent cycles. The are several gassing mechanisms in lithium-ion batteries, of which the primary source is through electrolyte reduction during the first cycle coinciding with the formation of the SEI layer on the anode surface. The gases generated during the formation of the SEI layer are degassed before the battery is sealed.

SUMMARY

Technical methods described herein provide a high throughput extraction of battery cell formation gas for analysis. In one exemplary embodiment, a battery cell is loaded into a sampling chamber of a degas station and an opening in the battery cell is created to release formation gas. A first portion of the formation gas can be routed to a collection chamber of the degas station while the formation gas is prevented from venting. After routing the first portion of the formation gas to the collection chamber, a second portion of the formation gas can be vented until degassing is complete. The first portion of the formation gas can be diluted with a dilution fluid and the diluted first portion of the formation gas can be routed to a cell quality control gas manifold configured to measure battery cell formation gas compositions.

In some embodiments, routing the first portion of the formation gas comprises actuating a plurality of valves to create a path between the sampling chamber and the collection chamber. In some embodiments, the battery cell is recovered from the sampling chamber after venting the second portion of the formation gas.

In another exemplary embodiment, the dilution fluid comprises air or an inert gas. In still other embodiments, creating the opening comprises activating an actuator to bring a piercing implement into contact with the battery cell.

In some embodiments, an expansion chamber is connected to the sampling chamber. In some embodiments, the expansion chamber comprises a configurable volume.

In yet another embodiment, a ratio of a volume of the sampling chamber to a volume of the collection chamber is selected to target a predetermined capture volume for formation gas. In some embodiments, the predetermined capture volume is 0.1 ml to 10 ml at normal temperature and pressure. In some embodiments, the first portion of the formation gas is diluted until a pressure setpoint is reached.

Aspects of the disclosure include a degas system for providing a high throughput extraction of battery cell formation gas. An exemplary system includes a sampling chamber configured to receive a battery cell. The sampling chamber can include an actuator operable to create an opening in the battery cell that releases formation gas. The system can further include a collection chamber coupled to the sampling chamber and a cell quality control gas manifold coupled to the collection chamber. The cell quality control gas manifold can be configured to measure battery cell formation gas compositions. The system further includes a plurality of valves operable to route a first portion of the formation gas to the collection chamber while the formation gas is prevented from venting. The plurality of valves are further operable to vent a second portion of the formation gas after routing the first portion of the formation gas to the collection chamber.

In some embodiments, the system further includes a dilution fluid source coupled to the collection chamber. In yet other embodiments, the dilution fluid comprises air or an inert gas. In still other embodiments, the plurality of valves is further operable to dilute the first portion of the formation gas with the dilution fluid. In some embodiments, the plurality of valves is further operable to route the diluted first portion of the formation gas to the cell quality control gas manifold.

In some embodiments, the actuator operable to create the opening in the battery cell is coupled to a piercing implement that, upon activation of the actuator, is brought into contact with the battery cell.

In some embodiments, the system further includes an expansion chamber coupled to the sampling chamber. The expansion chamber can include a configurable volume.

In some embodiments, a ratio of a volume of the sampling chamber to a volume of the collection chamber is selected to target a predetermined capture volume for formation gas. In yet other embodiments, the predetermined capture volume is 1 ml at normal temperature and pressure. In still other embodiments, the system includes a pressure transducer coupled to the collection chamber. The pressure transducer can be configured to ensure that the first portion of the formation gas is diluted until a pressure setpoint is reached.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which:

FIG. 3A illustrates a block diagram of the degas station of FIG. 2B after a process operation according to one or more embodiments;

FIG. 3B illustrates a block diagram of the degas station of FIG. 3A after a process operation according to one or more embodiments;

FIG. 4A illustrates a block diagram of the degas station of FIG. 3B after a process operation according to one or more embodiments;

FIG. 4B illustrates a block diagram of the degas station of FIG. 4A after a process operation according to one or more embodiments;

DETAILED DESCRIPTION

Figure 1:
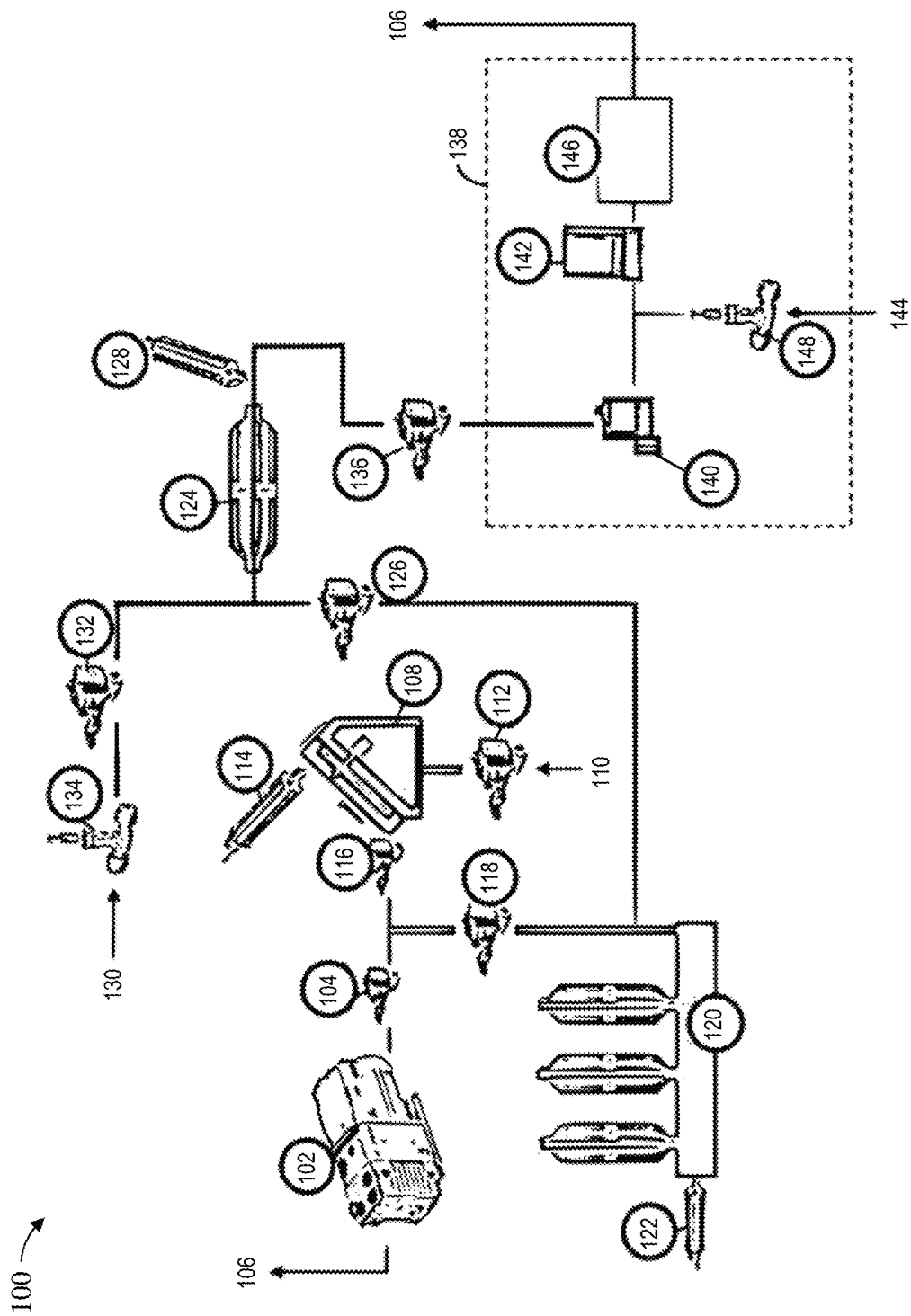
FIG. 1 illustrates a degas station configured for high throughput extraction and analysis of battery cell formation gas according to one or more embodiments.

The following description is merely exemplary in nature and is not intended to limit the present disclosure, its application or uses. It should be understood that throughout the drawings, corresponding reference numerals indicate like or corresponding parts and features.

The development of scalable, highly efficient next-generation lithium-ion battery manufacturing capabilities is critical to further advances in portable electronic devices and the implementation of high-efficiency electric vehicles. Generally, battery fabrication involves various steps including electrode production, cell production and conditioning, and testing/verification. The first stage in battery manufacturing is the fabrication of positive and negative electrodes and involves mixing, coating, drying, calendering, slitting, die cutting, and tab welding. Once completed the electrodes are assembled into cells and conditioned. The smallest unit of a lithium-ion cell includes two electrodes, a separator, and an ion-conductive electrolyte that fills the pores of the electrodes and the remaining space inside the cell.

Formation (also referred to as cell finishing) is the last step of cell production and generally refers to the first charging and discharging process of the battery cell. During formation, lithium ions are embedded in the crystal structure of the graphite on the anode side. The electrolyte decomposes upon the anode surface, resulting in the formation of a solid electrolyte interface (SEI) layer, which creates an interface layer between the electrolyte and the electrode.

After formation, the cell is conditioned (sometimes referred to collectively with formation as cell finishing). This process typically involves degassing, where gases released through electrolyte reduction during the first cycle coinciding with the formation of the SEI layer on the electrode surface are removed. During degassing, the cell pouch (bag) is pierced in a vacuum chamber and the escaping gases are allowed to vent. The cell is then sealed under vacuum.

After degassing and resealing, the battery cells can undergo various testing and quality verifications. These processes often involve aging, where cell characteristics and cell performance are monitored over a period of days or even weeks. Unfortunately, cell degradation and other quality issues discovered during or after aging will necessarily be somewhat delayed from the actual time of manufacturing due to the aging period.

Recently, development of cell quality control technology has turned to the analysis of the cell formation gas composition to infer quality properties of the cell prior to the aging process. Unfortunately, current battery fabrication processes are not compatible with high throughput means to acquire this formation gas. Consequently, formation gas analysis is typically carried out, if at all, in a batch type process for a subset (often very limited) of the cells in the production line and is not appropriate for use at scale.

One or more embodiments address one or more of the above-described shortcomings by providing novel degas equipment and process methodologies for high throughput extraction of battery cell formation gas. Rather than venting formation gas after cells are degassed and resealed, embodiments of the present disclosure modify the degas equipment to include a secondary vessel that captures the formation gas from the degas chamber prior to venting. The formation gas can then be diluted, and the diluted gas can be sampled in-line using a cell quality control gas manifold.

Technical solutions described herein facilitate a range of improvements to battery technology. As an initial matter, modifying the degas equipment to allow for formation gas to be captured, preprocessed, and delivered in-line to the quality control gas manifold enables highly scalable cell quality control technology prior to aging. Discovering cell quality issues pre-aging saves time and resources. Advantageously, the degas modifications made according to one or more embodiments requires only minimal changes to current manufacturing equipment and can be readily integrated within conventional manufacturing lines.

Other advantages are possible. Cell grading prior to module assembly is greatly improved. For example, embodiments of the present disclosure can be used to evaluate SEI formation gas composition and volume to reduce quality spills. Reducing quality spills frees up plant aging inventory space, as cells that would otherwise be scrapped can be removed prior to aging, thus reducing inventory hold times. This can enable, for example, improved efficiencies in the manufacture of next-generation, high-capacity lithium-ion batteries.

FIG. 1 illustrates a degas station 100 configured for the high throughput extraction and analysis of battery cell formation gas according to one or more embodiments. As shown in FIG. 1, the degas station 100 can include a vacuum pump 102 coupled to a first valve ("V1") 104 and an exhaust 106. The vacuum pump 102 can include any suitable equipment for providing vacuum to the degas station 100. As used herein, "vacuum" refers generally to near vacuum conditions and does not require perfect vacuum (0 Torr), but instead allows for low vacuum (about 10' Torr) to Ultra High Vacuum (about $10^{-11}$ Torr).

A sampling chamber 108 is coupled to an ambient air source 110 (also referred to as a chamber repressuring line)

via a second valve ("V2") 112. In some embodiments, the sampling chamber 108 includes a pressure transducer 114 configured to measure the vessel pressure of the sampling chamber 108. The sampling chamber 108 refers generally to the degas chamber or degas primary vessel within which a battery cell (not separately shown) is placed, pierced (sampled), and allowed to degas. In some embodiments, the sampling chamber 108 includes a linear actuator (not separately shown) coupled to a needle, blade, or other implement which can be activated to pierce the battery cell pouch, although other piercing mechanisms are within the contemplated scope of the disclosure. Output from the sampling chamber 108 is gated by a third valve ("V3") 116.

The first valve ("V1") 104 and the third valve ("V3") 116 are coupled to a common fourth valve ("V4") 118, which in turn is coupled to an expansion chamber 120. In some embodiments, the expansion chamber 120 includes a pressure transducer 122 configured to measure the vessel pressure of the expansion chamber 120. The sampling chamber 108 and the expansion chamber 120 can be referred to collectively as a degas vessel (or primary vessel).

The function of the expansion chamber 120 is to set the volume ratio of the sampling chamber 108 to the rest of the system (i.e., the degas station 100). In this manner, the degas station 100 can flexibly match the testing conditions in a current manufacturing line, where the manufacturing degas machine (not separately shown) chamber volume is known. In some embodiments, the volume of the sampling chamber 108 and/or the expansion chamber 120 can be changed to match the manufacturing degas machine chamber volume according to any desired volume ratio. For example, if the manufacturing degas machine chamber volume is 30000 ml and the desired volume ratio of 1:5, the sampling chamber 108 and the expansion chamber 120 can be scaled down to 1000 ml and 5000 ml, respectively. The sizing of collection vessels and selection of volume ratios is discussed in greater detail with respect to FIG. 6.

The sampling chamber 108 and the expansion chamber 120 are coupled to a collection chamber 124 via a common fifth valve ("V5") 126. In some embodiments, the collection chamber 124 includes a pressure transducer 128 configured to measure the vessel pressure of the collection chamber 124. The collection chamber 124 serves as a degas secondary vessel that is configured to receive formation gas from a degas primary vessel (e.g., the sampling chamber 108 and/or the expansion chamber 120) prior to venting, as described previously.

In some embodiments, the volume of the collection chamber 124 is sized to target a specific final capture volume of formation gas for analysis. In some embodiments, the targeted capture volume is 0.1 ml to 10 ml, for example 1 ml, of formation gas at normal temperature and pressure (NTP; approximately 1 atm pressure at 20 degrees Celsius). The sizing of collection vessels is discussed in greater detail with respect to FIG. 6.

The degas station 100 is generally described with respect to a single collection chamber 124 for ease of illustration and description, however, in some embodiments one or more additional collection vessels (not separately shown) are coupled to the outputs from valves 126 and a sixth valve ("V6") 132. In some embodiments, input to each collection vessel can be gated using dedicated input and output valves (not separately shown). In this manner an arbitrary number of collection vessels can be coupled in parallel with the degas station 100, although other configurations are within the contemplated scope of the disclosure.

In some embodiments, each of the collection vessels is built to a different degas volume specification. For example, a first collection vessel can be a 1 L vessel while a second collection vessel can be built to 0.2 L, 0.5 L, 0.8 L, 1.2 L, 1.5 L, 2 L, etc. In this manner a range of collection vessel volumes are available for degassing analysis. In some embodiments, a collection vessel is selected by routing formation gas via valves to a specific vessel while isolating the others, based on the degas conditions (e.g., cell sizes and gas generation volumes) of the present application. In this manner the targeted capture volume can be achieved over a range of cell sizes and gas generation volumes without modifying the degas station 100.

The fifth valve ("V5") 126 and the collection chamber 124 can be coupled to a compressed air source 130 (also referred to as bottle air) via the sixth valve ("V6") 132. The compressed air source 130 can include any suitable equipment for providing compressed air to the degas station 100. As used herein, "compressed air" refers generally to atmospheric air brought to a pressure above 1 atm, although ambient air is within the contemplated scope of the disclosure. In some embodiments, a flow regulator 134 gates the flowrate of air from the compressed air source 130 across the sixth valve ("V6") 132.

As further shown in FIG. 1, the output of the collection chamber 124 is coupled to a seventh valve ("V7") 136, which serves as the input gate to a cell quality control system 138. As shown, the cell quality control system 138 includes a flow controller 140, a flow meter 142, a carrier gas source 144, and a cell quality control gas manifold 146 (gas manifold), configured and arranged as shown. In some embodiments, a flow regulator 148 gates the flowrate of air from the carrier gas source 144.

The flow controller 140 can include any suitable equipment for flow control, such as, for example, a flow metering valve. The flow meter 142 can include any suitable equipment for measuring flow from the flow controller 140, such as, for example, high precision ultrasonic flow meters. The carrier gas source 144 can include any suitable equipment for providing a carrier gas to the degas station 100. As used herein, "carrier gas" refers generally to an inert gas (e.g., nitrogen or air) and can be pressured (brought above 1 atm) or atmospheric (1 atm).

The cell quality control gas manifold 146 includes equipment configured to analyze battery cell formation gas compositions and is not meant to be particularly limited. The cell quality control gas manifold 146 can include, for example, gas chromatography (GC) sensors or spectroscopy-based systems (e.g., mass spectroscopy, infrared spectroscopy, laser absorption spectroscopy, etc.). In some embodiments, the cell quality control gas manifold 146 is calibrated to receive a specific capture volume of formation gas. As discussed previously, in some embodiments, the targeted capture volume is 1 ml of formation gas at STP, although other calibrations are possible. In some embodiments, the cell quality control gas manifold 146 is coupled to the exhaust 106.

FIGS. 2A-5B and the accompanying description describe a degas station and a degassing scheme that ensures delivery of 1 ml (or any desired target capture volume) of formation gas at NTP to a cell quality control gas manifold.

Figure 2A:
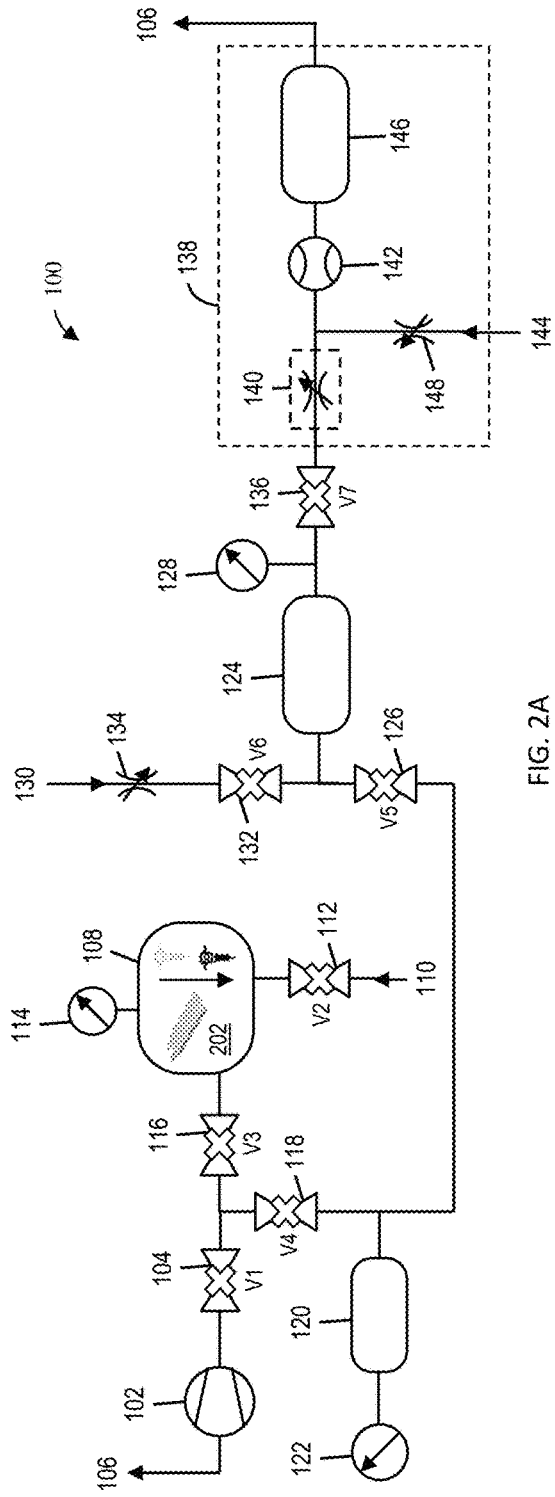
FIG. 2A illustrates a block diagram of a degas station configured for high throughput extraction and analysis of battery cell formation gas according to one or more embodiments.
Figure 2B:
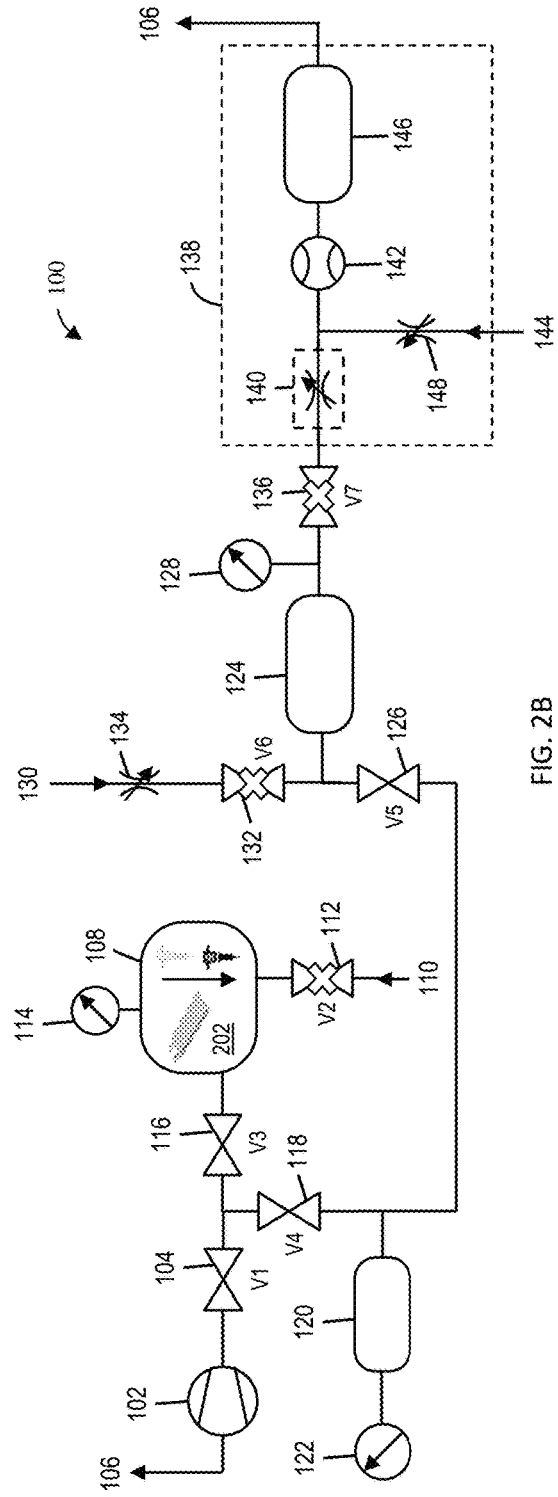
FIG. 2B illustrates a block diagram of the degas station of FIG. 2A after a process operation according to one or more embodiments.
Figure 5A:
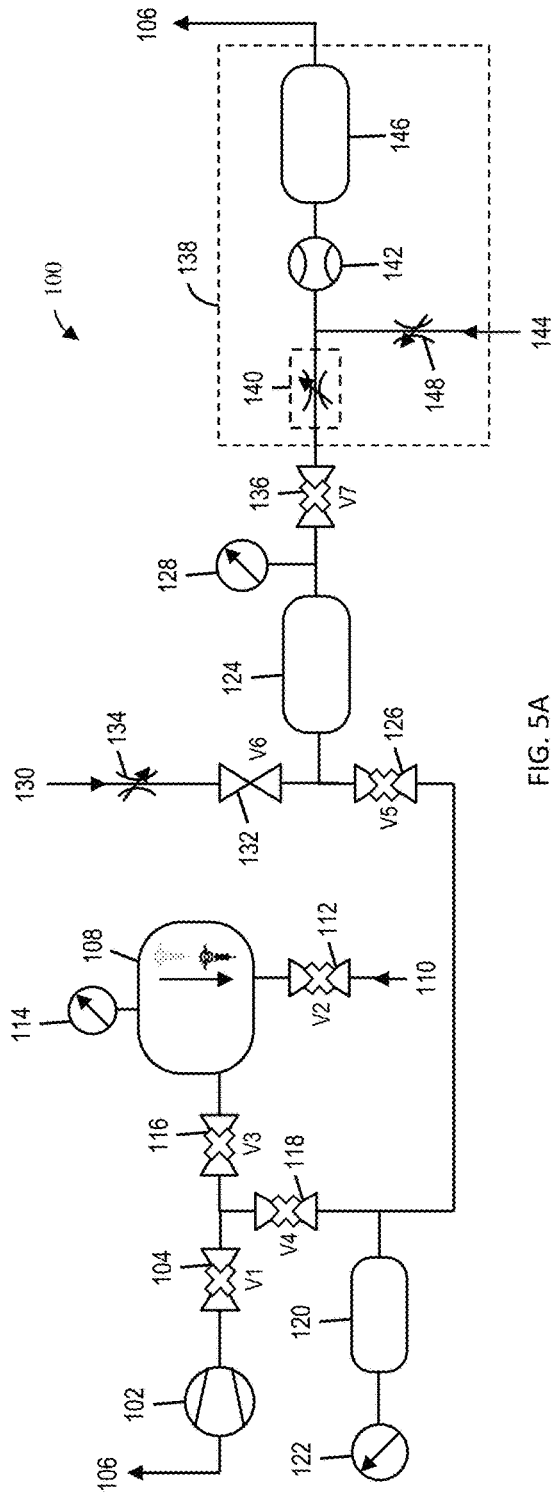
FIG. 5A illustrates a block diagram of the degas station of FIG. 4B after a process operation according to one or more embodiments.
Figure 5B:
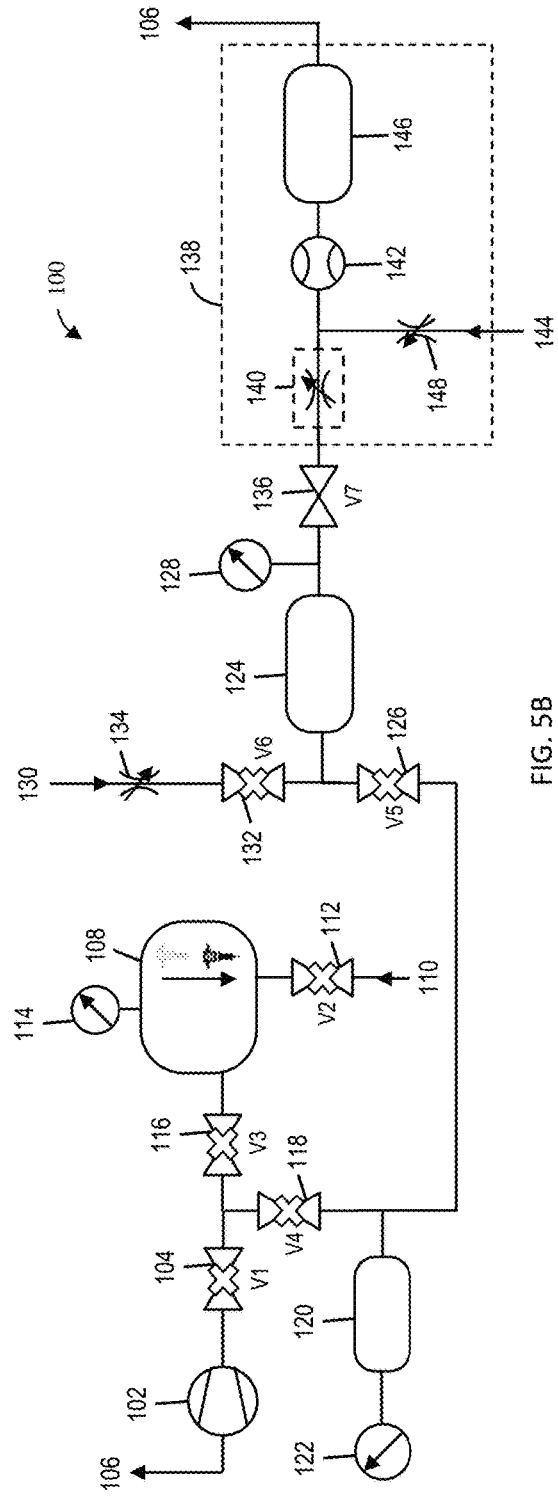
FIG. 5B illustrates a block diagram of the degas station of FIG. 5A after a process operation according to one or more embodiments.

FIG. 2A illustrates a block diagram of the degas station 100 configured for high throughput extraction and analysis of battery cell formation gas according to one or more embodiments. The block diagram shown in FIG. 2A depicts a simplified block diagram of portions of the degas station 100 shown in FIG. 1 at an initial state (Step 1) where a battery cell 202 is loaded into the sampling chamber 108 of the degas vessel. During this initial state all valves are closed (V1-V7 CLOSED) to isolate the various degas equipment.

At Step 2 (FIG. 2B), the degas vessel (e.g., the sampling chamber 108 and the expansion chamber 120) and the collection chamber 124 (and any of the additional collection chambers, if present) are evacuated. In some embodiments of the invention, evacuation is a two-step process. At Step 2A, valves 104, 116, 118, and 126 are opened (V1, V3, V4, and V5 OPEN) and the sampling chamber 108 is evacuated to "slit pressure". As used herein, "slit pressure" refers to a pressure that is sufficiently low to remove any residual gasses from the sampling chamber 108 but not low enough to burst the battery cell 202 pouch, for example, 5 psi below atmosphere. At Step 2B, valve 116 is closed to isolate the sampling chamber 108 and the remaining portions of the degas station 100 (e.g., expansion chamber 120 and collection chamber 124) are brought to the final evacuation pressure (final vacuum pressure). During this state the expansion chamber 120 and the collection chamber 124 are under vacuum due to exposure to the vacuum pump 102. While isolated, the battery cell 202 is slit or otherwise pierced (Step 3) under slit pressure (preventing pouch rupture/burst due to an excessive internal/external pressure differential). Once the battery cell 202 is slit, formation gas exits the battery cell 202 and fills the sampling chamber 108. At Step 4, valves 104 and 126 are closed and valve 116 is then opened (V3 OPEN), allowing gas to expand into the expansion chamber 120. This causes the pressure in the expansion chamber 120 to increase. Steps 3 and 4 are not separately illustrated.

At Step 5 (FIG. 3A), valves 116, 118, and 126 are opened (V3, V4, and V5 OPEN) and the sampling chamber 108, the expansion chamber 120, and the collection chamber 124 are allowed to come to equilibrium. During this phase the formation gas expands into the collection chamber 124 until equilibrium pressure is achieved. After gas collection is complete all valves are closed (V1-V7 CLOSED) at Step 6 (not separately shown).

At Step 7 (FIG. 3B), valves 104, 116, and 118 are opened (V1, V3, and V4 OPEN) and the sampling chamber 108 and the expansion chamber 120 are allowed to complete the degassing process. During this phase the remaining formation gas is vented via the vacuum pump 102 through the exhaust 106. Notably, the formation gas within the collection chamber 124 is isolated from the vacuum pump 102 due to closure of the valve 126 ("V5"). In some embodiments, the battery cell 202 is sealed after degassing. After degassing is complete all valves are closed (V1-V7 CLOSED) at Step 8 (not separately shown).

At Step 9 (FIG. 4A), valves 112, 116, and 118 are opened (V2, V3, and V4 OPEN) and the sampling chamber 108 and the expansion chamber 120 are filled with air via the ambient air source 110. In some embodiments, the sampling chamber 108 and the expansion chamber 120 are brought to normal pressure (1 atm), although other refill pressures are possible.

At Step 10 (FIG. 4B), all valves are closed (V1-V7 CLOSED) and the battery cell 202 is recovered. In some embodiments, the battery cell 202 is finalized using known processes (e.g., aging, initial cycling, etc.).

At Step 11 (FIG. 5A), valve 132 is opened (V6 OPEN) and the formation gas in the collection chamber 124 is diluted with air via the compressed air source 130. In some embodiments, the collection chamber 124 is brought to a predetermined pressure setpoint, such as, for example, 1.25 atm, although other pressure setpoints are possible. The calculation of pressure setpoints for a given application is discussed in greater detail with respect to FIG. 6. After dilution is complete all valves are closed (V1-V7 CLOSED) at Step 12 (not separately shown).

At Step 13 (FIG. 5B), valve 136 is opened (V7 OPEN) and the diluted formation gas in the collection chamber 124 can enter the cell quality control system 138. In some embodiments, the flow controller 140 and the flow meter 142 precisely gate the release of the diluted formation gas. In some embodiments, the carrier gas source 144 (notably separate from the compressed air source 130 to ensure isolation and prevent contamination) provides a carrier gas (e.g., air, nitrogen, etc.) under constant pressure to deliver the diluted formation gas to the cell quality control gas manifold 146.

Once delivered, the cell quality control gas manifold 146 can determine the diluted formation gas composition as discussed previously. In some embodiments, the diluted formation gas composition is compared to a database or other record of reference compositions to infer a quality of the battery cell 202. A database can be built empirically or experimentally (or both) by recording formation gas compositions and ultimate quality control outcomes using conventional processes (i.e., after aging and/or cycling, etc.). In this manner the quality of the battery cell 202 can be inferred prior to completing the aging process.

As discussed previously, the appropriate size (volume) of the collection chamber can be selected to target a predetermined desired capture volume for formation gas. To reliably capture 1 ml of formation gas at STP, several input parameters are required: the volume of the degas vessel (L), the size of the battery cell (Ah), the gas generation for the specific battery cell chemistry (ml/Ah), and the relationship between degas vessel volume, collection chamber volume, and percent gas capture.

By means of example only, consider a manufacturing specification stating that two 100 Ah cells de-gassed in a 154 L degas vessel to provide a gas generation of 6 ml/5Ah. Under these conditions, gas generation will be approximately 240 ml (200 Ah*6 ml/5 Ah) at a concentration of 1.56 ml/L (240 ml/154 L) for the respective cells. Consider further that for a degas vessel volume of 4 L (other sizes are possible) the formation gas volume will be approximately 6.24 ml (1.56*4). Accordingly, for a targeted capture of 1 ml formation gas, we must achieve a gas capture of 16 percent (1/6.24). A 1 ml formation gas target is used for illustrative purposes only; it is understood that any capture volume can be targeted.

Figure 6:
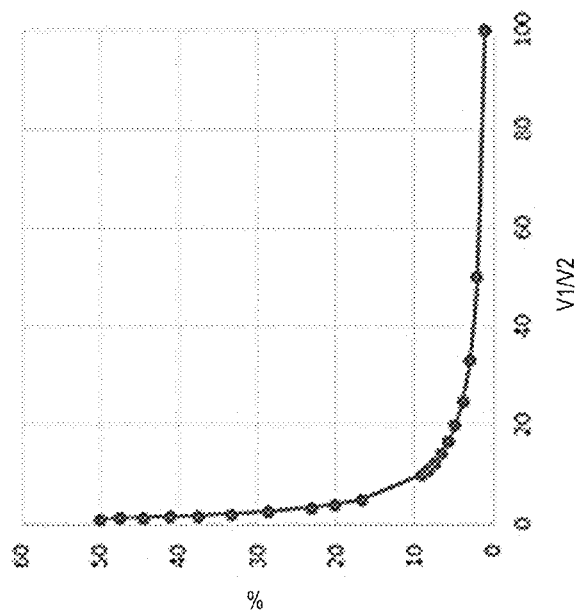
FIG. 6 illustrates a relationship between gas captured and the volume ratio of a degas chamber and a collection vessel according to one or more embodiments.

To achieve 16 percent gas capture, the relationships among the volume parameters (degas vessel volume and collection chamber volume) and percent gas capture must be understood. FIG. 6 describes the relationship between the volume parameters and the percent gas capture. As shown in FIG. 6, percent gas captured changes with respect to the volume ratio (V1/V2) of the degas vessel volume (V1) to the collection chamber volume (V2). From inspection, 16 percent gas capture corresponds to a volume ratio of approximately 5. Assuming a degas vessel volume of 4 L (this will be known for a given application and need not be limited to 4 L), the collection vessel volume should be 800 ml for 16 percent gas capture.

Once the collection chamber volume is determined, the predetermined pressure setpoint for sampling (refer to FIG. 5A) can be calculated. In some embodiments, the pressure setpoint is determined rigorously using, for example, computational fluid dynamics (CFD). In some embodiments, a few assumptions are taken to ease calculation. Assumptions can include, for example, that the formation gas is an ideal gas of pure ethylene under isothermal conditions with negligible line volume (i.e., line volume<<total volume of degas vessel and collection chamber).

Under these assumptions the formation gas molar loads and the predetermined pressure setpoint for sampling can be determined analytically. In the degas vessel, 6 ml of ethylene gas collected at NTP for one 5 Ah cell represents $2.44 \times 1^{-4}$ mol ethylene gas ($n_{gas}$). In the collection chamber, the mol equivalent of 1 ml of ethylene gas at NTP ($n_{secondary}$) is given by $(PV_2)/RT$ and, for the present example, is $4.06 \times 10^{-5}$ mol, where P is the equilibrated pressure of the degas chamber and collection chamber 124 in step 5 (FIG. 3A), V2 is the volume of the collection chamber 124, R is the ideal gas constant, and T is temperature in degrees Kelvin.

Once $n_{gas}$ is known, the predetermined pressure setpoint ($P_{SP}$) can the determined for any desired dilution ratio (e.g., 1000:1 v/v, 100:1 v/v, 10:1 v/v, etc.) according to the formula $P_{SP}=(n_{gas}+n_{air})RT/V_2$. Assuming a desired dilution ratio of 1000:1 (air:gas, v/v), $P_{SP}$ is approximately 3.65 psig (1.25 atm absolute).

Gas collection pressures can also be calculated. Pressure in the degas chamber ($P_1$) can be determined from the ideal gas law ($P_1=n_{gas}RT/V_1$) and, for the present example, $P_1=151$ Pa. Combined pressure ($P_3$) in the degas vessel and collection chamber is given by $P_3=(P_1V_1)/(V_1+V_2)$ and, for the present example, $P_3=137.5$ Pa.

Figure 7A:
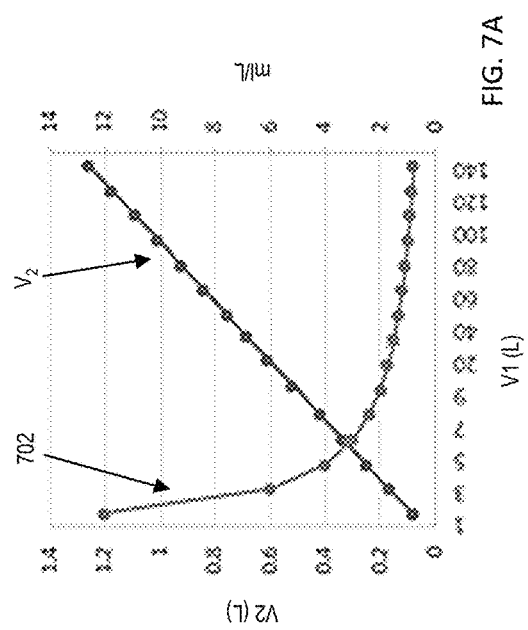
FIG. 7A illustrates the relationship between degas vessel volume, collection chamber volume, and gas concentration when cell size is fixed according to one or more embodiments.

To collect 1 ml of formation gas at NTP, FIG. 7A illustrates the relationship between degas vessel volume ($V_1$), collection chamber volume ($V_2$), and gas concentration (ml/L) when cell size is fixed (e.g., at 100 Ah) according to one or more embodiments. From inspection, collection chamber volume ($V_2$) increases linearly with increasing degas vessel volume ($V_1$). Conversely, gas concentration 702 initially decreases rapidly with increasing degas vessel volume ($V_1$) before somewhat stabilizing for large degas vessel volumes (e.g., above 100 L).

Figure 7B:
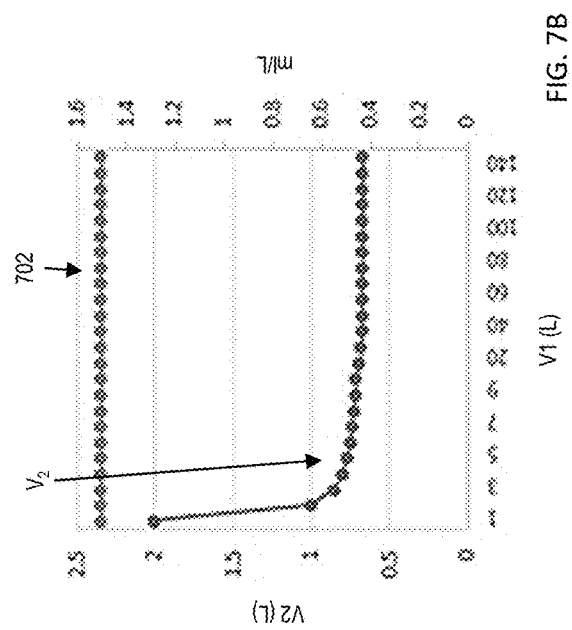
FIG. 7B illustrates the relationship between degas vessel volume, collection chamber volume, and gas concentration when cell size is proportional to the degas chamber volume according to one or more embodiments.

To collect 1 ml of formation gas at NTP, FIG. 7B illustrates the relationship between degas vessel volume ($V_1$), collection chamber volume ($V_2$), and gas concentration (ml/L) when cell size is proportional to the degas vessel volume according to one or more embodiments. From inspection, gas concentration 702 is constant (e.g., approximately 1.5 ml/L) over a wide range of degas vessel volumes ($V_1$). Conversely, collection chamber volume ($V_2$) decreases rapidly until approximately 3 L before somewhat stabilizing over larger degas vessel volumes (e.g., above 10 L).

Figure 8:
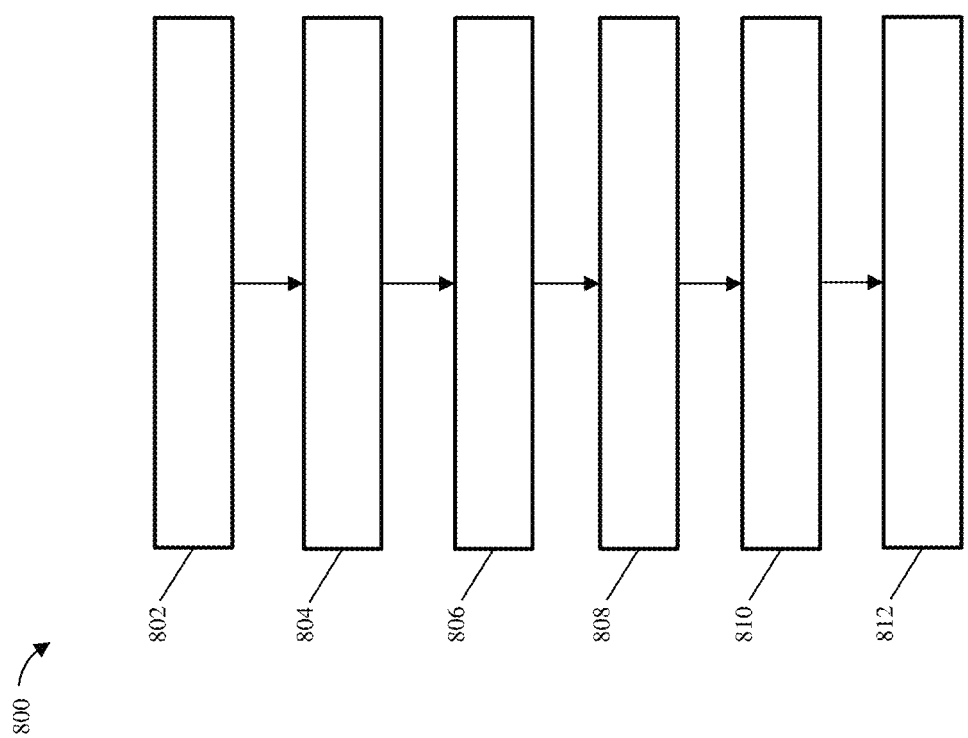
FIG. 8 is a flowchart in accordance with one or more embodiments.

Referring now to FIG. 8, a flowchart 800 for providing high throughput extraction and analysis of battery cell formation gas is generally shown according to an embodiment. The flowchart 800 is described in reference to FIGS. 1-7B and may include additional steps not depicted in FIG. 8. Although depicted in a particular order, the blocks depicted in FIG. 8 can be rearranged, subdivided, and/or combined.

At block 802, a battery cell is loaded into a sampling chamber of a degas station. In some embodiments, the degas station (e.g., degas vessel, sampling chamber, and transfer lines to collection vessel) are evacuated prior to loading a new battery cell (e.g., in Steps 2 and 7 shown in FIGS. 2B and 3B). At block 804, an opening is created in the battery cell to release formation gas. In some embodiments, the opening is a slit created by piercing the battery cell. In some embodiments, creating the opening comprises activating an actuator to bring a piercing implement into contact with the battery cell pouch.

At block 806, a first portion of the formation gas is routed to a collection chamber of the degas station while the formation gas is prevented from venting. In some embodiments, routing the first portion of the formation gas comprises actuating a plurality of valves to create a path between the sampling chamber and the collection chamber.

At block 808, a second portion of the formation gas is vented after routing the first portion of the formation gas to the collection chamber. In some embodiments, the battery cell is recovered from the sampling chamber after venting the second portion of the formation gas.

At block 810, the first portion of the formation gas is diluted with a dilution fluid. In some embodiments, the dilution fluid comprises air or an inert gas. At block 812, the diluted first portion of the formation gas is routed to a cell quality control gas manifold configured to measure battery cell formation gas compositions.

In some embodiments, an expansion chamber is connected to the sampling chamber. In yet other embodiments, the expansion chamber comprises a configurable volume.

In some embodiments, a ratio of a volume of the sampling chamber to a volume of the collection chamber is selected to target a predetermined capture volume for formation gas. In some embodiments, the predetermined capture volume is 0.1 ml to 10 ml at normal temperature and pressure. In some embodiments, the predetermined capture volume is 1 ml at normal temperature and pressure. In some embodiments, the first portion of the formation gas is diluted until a pressure setpoint is reached.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof

What is claimed is:

1. A method for extracting battery cell formation gas, the method comprising:
   loading a battery cell in a sampling chamber of a degas station;
   completing a two-step evacuation process comprising a first step and a second step, the first step comprising bringing the sampling chamber and a collection chamber of the degas station to a slit pressure for the battery cell, the second step comprising isolating the sampling chamber and bringing the collection chamber to a vacuum pressure lower than the slit pressure;
   creating an opening in the battery cell to release formation gas at the slit pressure;
   routing a first portion of the formation gas to the collection chamber while the formation gas is prevented from venting, the collection chamber comprising a volume selected to achieve a predetermined capture volume for formation gas, the volume determined from a curve describing a predetermined relationship between a volume ratio of the sampling chamber to the collection chamber and a gas capture rate for the formation gas, the gas capture rate determined from a ratio of the predetermined capture volume and a formation gas volume for the battery cell;
   after routing the first portion of the formation gas to the collection chamber, venting a second portion of the formation gas;

diluting the first portion of the formation gas with a dilution fluid; and routing the diluted first portion of the formation gas to a cell quality control gas manifold configured to measure battery cell formation gas compositions.

2. The method of claim 1, wherein routing the first portion of the formation gas comprises actuating a plurality of valves to create a path between the sampling chamber and the collection chamber.

3. The method of claim 1, wherein the dilution fluid comprises air or an inert gas.

4. The method of claim 1, further comprising recovering the battery cell from the sampling chamber after venting the second portion of the formation gas.

5. The method of claim 1, wherein creating the opening comprises activating an actuator to bring a piercing implement into contact with the battery cell.

6. The method of claim 1, further comprising connecting an expansion chamber to the sampling chamber.

7. The method of claim 6, wherein the expansion chamber comprises a configurable volume.

8. The method of claim 1, wherein the predetermined capture volume is 0.1 ml to 10 ml at normal temperature and pressure.

9. The method of claim 1, wherein the first portion of the formation gas is diluted until a pressure setpoint is reached.

10. A degas system for extracting battery cell formation gas, the system comprising:
a sampling chamber configured to receive a battery cell, the sampling chamber comprising an actuator operable to create an opening in the battery cell that releases formation gas;
a collection chamber coupled to the sampling chamber, the collection chamber comprising a volume selected to achieve a predetermined capture volume for formation gas, the volume determined from a curve describing a predetermined relationship between a volume ratio of the sampling chamber to the collection chamber and a gas capture rate for the formation gas, the gas capture rate determined from a ratio of the predetermined capture volume and a formation gas volume for the battery cell;
a cell quality control gas manifold coupled to the collection chamber, the cell quality control gas manifold configured to measure battery cell formation gas compositions; and
a plurality of valves operable to route a first portion of the formation gas to the collection chamber while the formation gas is prevented from venting, the plurality of valves further operable to vent a second portion of the formation gas after routing the first portion of the formation gas to the collection chamber.

11. The system of claim 10, further comprising a dilution fluid source coupled to the collection chamber.

12. The system of claim 11, wherein the plurality of valves is further operable to dilute the first portion of the formation gas with the dilution fluid.

13. The system of claim 12, wherein the plurality of valves is further operable to route the diluted first portion of the formation gas to the cell quality control gas manifold.

14. The system of claim 12, wherein the dilution fluid comprises air or an inert gas.

15. The system of claim 10, wherein the actuator operable to create the opening in the battery cell is coupled to a piercing implement that, upon activation of the actuator, is brought into contact with the battery cell.

16. The system of claim 10, further comprising an expansion chamber coupled to the sampling chamber, the expansion chamber comprising a configurable volume.

17. The system of claim 10, wherein the predetermined capture volume is 0.1 ml to 10 ml at normal temperature and pressure.

18. The system of claim 17, further comprising a pressure transducer coupled to the collection chamber, the pressure transducer configured to ensure that the first portion of the formation gas is diluted until a pressure setpoint is reached.

* * * * *